(12) United States Patent
Cook et al.

(10) Patent No.: US 7,705,314 B2
(45) Date of Patent: Apr. 27, 2010

(54) METHOD AND APPARATUS FOR PET TIME OF FLIGHT GENERATION OF COMPRESSION SINOGRAM AND IMAGE RECONSTRUCTION

(75) Inventors: Michael Joseph Cook, Oconomowoc, WI (US); Mark William Wille, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 157 days.

(21) Appl. No.: 11/447,558

(22) Filed: Jun. 6, 2006

(65) Prior Publication Data

US 2007/0278409 A1 Dec. 6, 2007

(51) Int. Cl.
G01T 1/66 (2006.01)
G06K 9/66 (2006.01)

(52) U.S. Cl. .............. 250/363.04; 250/370.09; 382/232; 382/233

(58) Field of Classification Search ........ None
See application file for complete search history.

(56) References Cited

U.S. PATENT DOCUMENTS

| | | | |
|---|---|---|---|
| 6,215,903 B1 | 4/2001 | Cook | 382/232 |
| 7,050,639 B1 * | 5/2006 | Barnes et al. | 382/239 |
| 2003/0035884 A1 * | 2/2003 | Gluschenkov et al. | 427/8 |
| 2003/0228041 A1 * | 12/2003 | Bae et al. | 382/131 |
| 2004/0222379 A1 * | 11/2004 | Cook | 250/363.03 |
| 2007/0040122 A1 * | 2/2007 | Manjeshwar et al. | 250/363.03 |
| 2007/0201611 A1 * | 8/2007 | Pratx et al. | 378/4 |
| 2007/0230829 A1 * | 10/2007 | Sirohey et al. | 382/299 |

OTHER PUBLICATIONS

"Zone Cache Histogramming Technique for Performing Histogramming of Non-ordered/Random Event Stream", Jan. 25, 2006, IP.com (online)[retrieved Mar. 3, 2004].Retrieved from: IP.com Prior Art Database. IP.com number: IPCOM000133358D.*

Abott et al., "A High-Performance VME-Based Acquisition System for Positron Emission Mammography", Nuclear Science Symposium Conference Record, 2001, IEEE, Vol. 4, Nov. 4-10, 2001, pp. 1947-1951.*

* cited by examiner

*Primary Examiner*—David P Porta
*Assistant Examiner*—Yara B Green
(74) *Attorney, Agent, or Firm*—ZPS Group, SC

(57) ABSTRACT

A method for reducing a need for physical memory includes compressing a sub-region of an intermediate histogram to obtain a compressed result, and storing the compressed result in a physical or virtual file.

22 Claims, 8 Drawing Sheets

ZONE CACHE HISTOGRAMMING PET COINCIDENCE EVENT STREAM PROCESSING

METHOD AND APPARATUS FOR PET TIME OF FLIGHT GENERATION OF COMPRESSION SINOGRAM AND IMAGE RECONSTRUCTION

BACKGROUND OF THE INVENTION

The present invention relates generally to medical imaging, and more particularly to a histogrammer for a medical imaging device such as a positron emission tomography scanner.

A positron emission tomography (PET) scanner detects gamma rays which emanate from the patient. In a PET scan, the patient is initially injected with a radiopharmaceutical, which is a radioactive substance such as FDG ([$^{18}$F] fluorodeoxyglucose) which emits positrons as it decays. Once injected, the radiopharmaceutical becomes involved in certain known bodily processes such as glucose metabolism or protein synthesis, for example. The emitted positrons travel a very short distance before they encounter an electron, at which point an annihilation event occurs whereby the electron and positron are annihilated and converted into two gamma rays. Each of the gamma ray has an energy of 511 keV, and the two gamma rays are directed in nearly opposite directions. The two gamma rays are detected essentially simultaneously by two of the detector crystals (also commonly referred to as "scintillators" or "scintillator crystals") in the PET scanner, which are arranged in rings around the patient bore. The simultaneous detection of the two gamma rays by the two detector crystals is known as a "coincidence event." The millions of coincidence events which are detected and recorded during a PET scan are used to determine where the annihilation events occurred and to thereby reconstruct an image of the patient.

Part of the data acquisition and image reconstruction process involves generating a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan the data in the histogram are used to reconstruct the image of the patient. The completed histogram containing all the data from the scan is commonly referred to as a "result histogram." The term "histogrammer" generally refers to the components of the scanner, e.g., processor and memory, which carry out the function of creating the histogram.

As PET scanner technology advances, e.g., as detector crystals become faster and as PET scanners include greater numbers of detector crystals, the desired data acquisition bandwidth increases. This increase places greater demands on the histogrammer. In general terms, the function of a histogrammer is to segregate and count events of a multi-type event stream, providing individual counts for each unique event type. For each event in the event stream, the histogrammer reads the current count value in a cell of the histogram, modifies the count value by incrementing or decrementing it, and writes the modified value back to the cell. In current PET scanners, the histogrammer may be required to process millions of events per second. Next generation PET scanners will likely place even higher demands on the speed and memory utilization of the histogramming function. The present invention addresses these needs.

Additionally, it is conjectured that high resolution Positron Emission Tomography (PET) Time Of Flight (TOF) information can be used to improve the image quality of images produced from PET acquisitions. Time of Flight refers to the time difference in detection of the two gamma rays that were produced from a given positron annihilation. TOF is relative to the detector ring diameter and the location of the positron annihilation within the scan field of view. PET detector and acquisition electronics timing resolution have progressed such that sub-nanosecond resolution time of flight difference measurement is achievable and argumentatively clinically cost effective.

PET raw data is nominally collected in sinogram/projection based Line Of Responses (LORs) histograms to compress the acquired data and enhance the performance of the image reconstruction process. The conventional non-TOF PET sinogram/projection based raw data can routinely exceed 64 megabytes per acquisition (frame) and hundreds of megabytes per scan in the Dynamic and/or Gated scan modes. TOF PET adds another dimension to the sinograms/projections, and consequently the sinogram raw data size produced in the Dynamic and/or Gated scan modes would scale by the TOF dimension width (minimally anticipated to be in the range of 32-64) and exceed hundreds of gigabytes and require significant increase in physical memory if current deployed techniques were continued for TOF acquisitions. This could add substantial cost for physical memory to the PET acquisition subsystem and result in an order of magnitude increase in reconstruction processing.

Due to the anticipated reconstruction processing hit and costly increase of Random Access Memory (RAM) projected for TOF sinogram/projection based live event stream histogramming, alternative acquisition methods and raw data formats are being considered industry-wide. Unlike the methods and apparatus disclosed herein, the proposals made to date will most likely have the negative affect on reconstruction time and/or increase the time from end of acquisition until images are presented for medical diagnosis.

The methods and apparatus described herein to produce Compressed Time Of Flight Sinograms for a live or unlist PET TOF coincidence event stream can greatly reduce the amount of physical memory required, and furthermore present the raw data to the image reconstruction process in a LOR ordered format that would significantly reduce the processing time from end of acquisition to presentation of the corresponding images.

BRIEF DESCRIPTION OF THE INVENTION

In one aspect, a method for reducing a need for physical memory includes compressing a sub-region of an intermediate histogram to obtain a compressed result, and storing the compressed result in a physical or virtual file.

In another aspect, a PET system includes an imaging volume configured to receive an object to be scanned, at least one gamma camera positioned to receive at least one gamma ray emitted from the object, and a computer coupled to the gamma camera. Wherein the computer is configured to generate a compressed PET time of flight sinogram, and reconstruct a TOF image using the compressed PET TOF sinogram.

In still another aspect, a PET system includes an imaging volume configured to receive an object to be scanned, at least one gamma camera positioned to receive at least one gamma ray emitted from the object, and a computer coupled to the gamma camera. Wherein the computer is configured to use a Removal of Initial Value Nibbles (RIVN) based compression algorithm and a ZCH algorithm for intermediate histogrammer processing steps.

In yet another aspect, a method includes processing a list of PET events in a single pass wherein the resultant histogram includes TOF information.

In still another aspect, a method includes processing a list of events in a single pass, wherein the list has at least one million events.

DETAILED DESCRIPTION OF THE INVENTION

Figure 1:
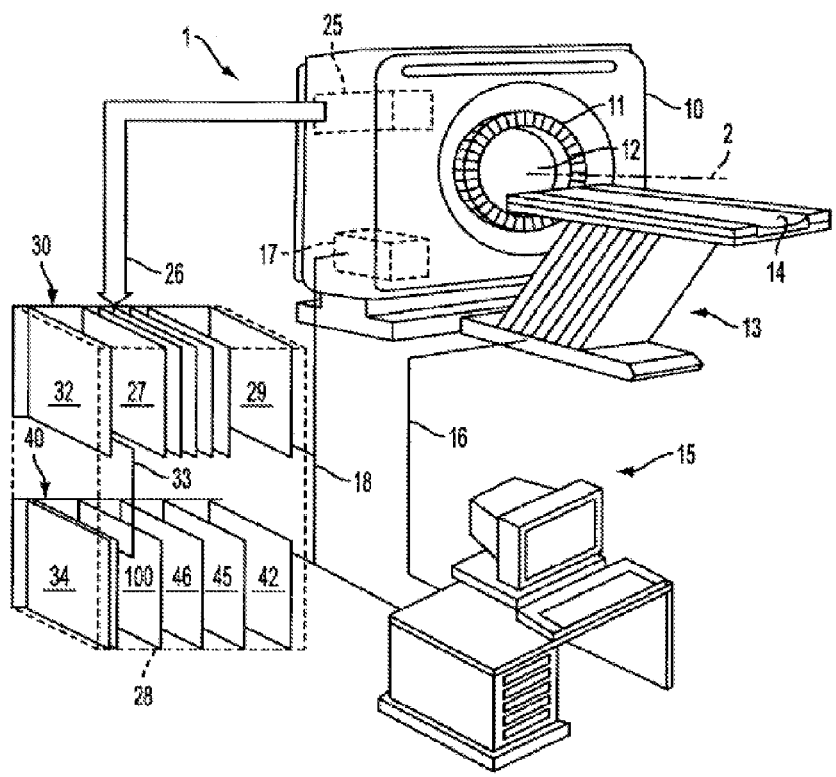
FIG. 1 is a drawing of an imaging system according an exemplary embodiment of the invention.

FIG. 1 illustrates a PET scanner 1 which includes a gantry 10 supporting a detector ring assembly 11 about a central opening or bore 12. The detector ring assembly 11 is circular in shape and is made up of multiple detector rings (not shown) that are spaced along a central axis 2 to form a cylindrical detector ring assembly. According to one embodiment, the detector ring assembly 11 includes 24 detector rings spaced along the central axis 2. A patient table 13 is positioned in front of the gantry 10 and is aligned with the central axis 2 of the detector ring assembly 11. A patient table controller (not shown) moves the table bed 14 into the bore 12 in response to commands received from an operator work station 15 through a communications link 16. A gantry controller 17 is mounted within the gantry 10 and is responsive to commands received from the operator work station 15 through a second communication link 18 to operate the gantry.

Figure 2:
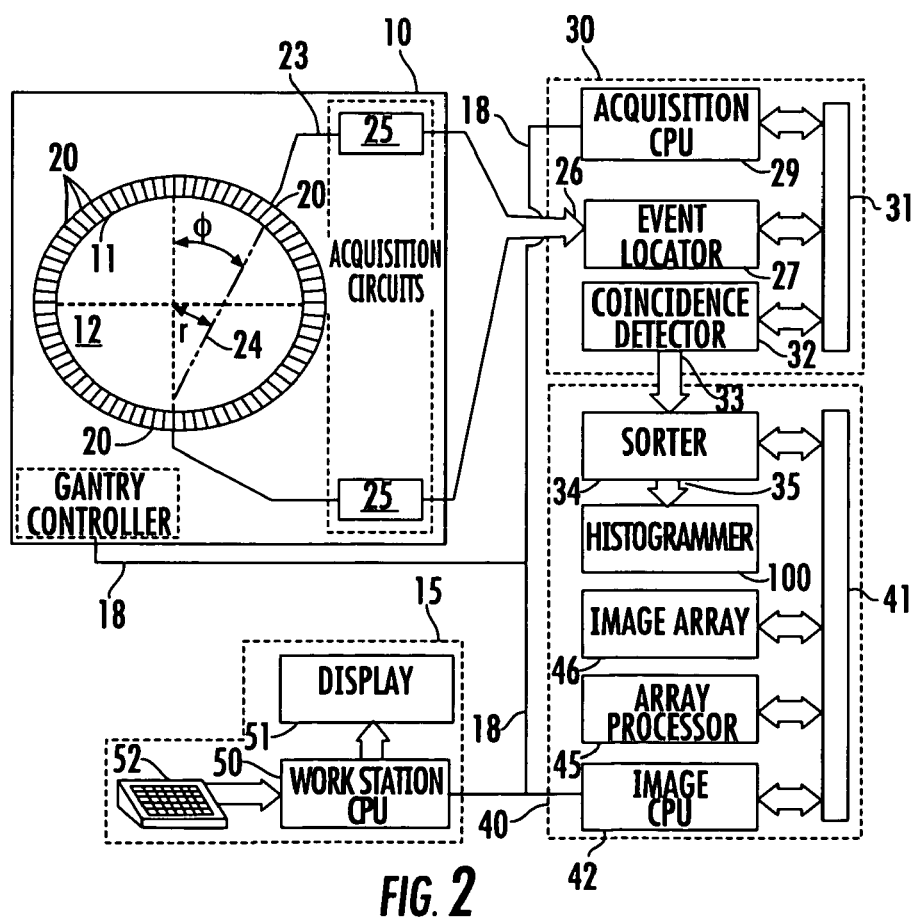
FIG. 2 is a schematic diagram of the imaging system of FIG. 1.

As shown in FIG. 2, the operator work station 15 includes a central processing unit (CPU) 50, a display 51, and a keyboard 52. Through the keyboard 52 and associated control panel switches, the operator can control the calibration of the PET scanner, its configuration, and the positioning of the patient table for a scan. Similarly, the operator can control the display of the resulting image on the display 51 and perform image enhancement functions using programs executed by the work station CPU 50.

Figure 4:
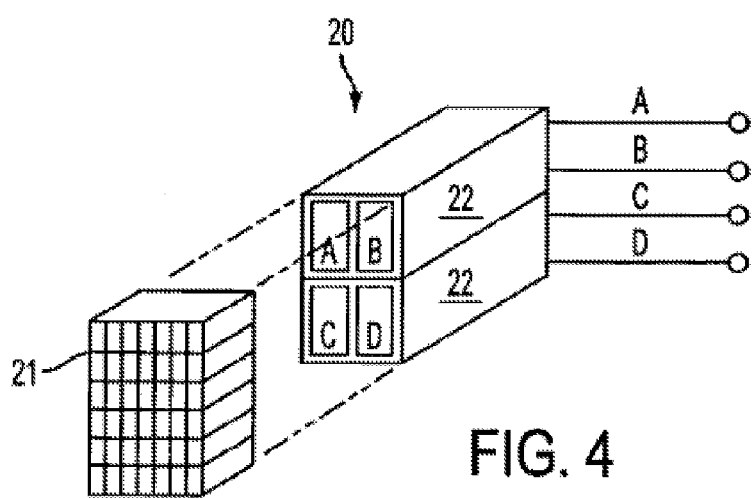
FIG. 4 is a drawing of a detector block which forms part of the PET scanner of FIG. 1.

The detector ring assembly 11 is comprised of a number of detector modules. According to one embodiment, the detector ring assembly 11 comprises 36 detector modules, where each detector module comprises eight detector blocks. An example of one detector block 20 is shown in FIG. 4. The eight detector blocks 20 in a detector module can be arranged in a 2*4 configuration such that the circumference of the detector ring assembly 11 is 72 detector blocks around, and the width of the detector ring 11 assembly is 4 detector blocks wide. Each detector block 20 typically comprises a number of individual detector crystals. For example, as shown in FIG. 4, each detector block 20 may comprise a 6*6 matrix of 36 detector crystals 21. The detector ring assembly 11 would thus have 24 detector rings. Each ring would have 432 detector crystals.

Each detector crystal 21 may comprise a scintillator formed, for example, of lutetium oxyorthosilicate (LSO) or lutetium-yttrium oxyorthosilicate (LYSO) or the like. The 36 detector crystals in the block 20 are disposed in front of four photomultiplier tubes (PMTs) 22. Each PMT 22 produces an analog signal on one of the lines A-D shown in FIG. 4 which rises sharply when a scintillation event occurs then tails off exponentially. The position in the 6*6 detector crystal matrix at which the scintillation event took place determines the relative magnitudes of the analog signals, and the energy of the gamma ray which caused the event determines the total magnitude of these signals.

As shown in FIG. 2, a set of acquisition circuits 25 is mounted within the gantry 10 to receive the four signals from each of the detector blocks 20 in the detector ring assembly 11. The acquisition circuits 25 determine the event coordinates within the block of detector crystals 21 by comparing the relative signal strengths as follows:

$$x=(A+C)/(A+B+C+D)$$

$$z=(A+B)/(A+B+C+D)$$

These coordinates (x,z), along with the sum of all four signals (A+B+C+D) are then digitized and sent through a cable 26 to an event locator circuit 27 housed in a separate cabinet 28. Each acquisition circuit 25 also produces an event detection pulse (EDP) which indicates the exact moment the scintillation event took place. Of course, the above-described configuration of detector crystals, detector blocks, and detector modules is merely an example. Other configurations, scintillators, sizes, and numbers of detector crystals, blocks, and modules can be used, as will be appreciated by those skilled in the art.

The event locator circuits 27 form part of a data acquisition processor 30 which periodically samples the signals produced by the acquisition circuits 25. The data acquisition processor 30 has an acquisition CPU 29 which controls communications on the local area network 18 and a bus 31. The event locator circuits 27 assemble the information regarding each valid event into a set of digital numbers that indicate precisely when the event took place and the position of the detector crystal 21 which detected the event. The event data packets are transmitted to a coincidence detector 32 which is also part of the data acquisition processor 30.

The coincidence detector 32 accepts the event data packets from the event locator circuits 27 and determines if any two of them are in coincidence. Coincidence is determined by a number of factors. First, the time markers in each event data packet must be within a specified time period of each other, e.g., 12.5 nanoseconds, and second, the locations indicated by the two event data packets must lie on a straight line which passes through the field of view (FOV) in the scanner bore 12. Events which cannot be paired are discarded, but coincident event pairs are located and recorded as a coincidence data packet that is transmitted through a serial link 33 to a sorter 34. The format of the coincidence data packet may be, for example, a multi bit data stream which includes, among other things, digital numbers that precisely identify the locations of the two detector crystal 21 pairs that detected a given event. For a detailed description of an example of a coincidence detector 32, reference is made to U.S. Pat. No. 5,241,181 entitled "Coincidence Detector For A PET Scanner."

The sorter 34, which may comprise a CPU and which forms part of an image reconstruction processor 40, receives the coincidence data packets from the coincidence detector 32. The function of the sorter 34 is generally to receive the coincidence data packets and to generate from them memory addresses for the efficient storage of the coincidence data. The sorter 34 outputs a stream of histogram events to a histogrammer 100 downstream of the sorter via an interconnect 35 such as a memory bus.

Figure 3:
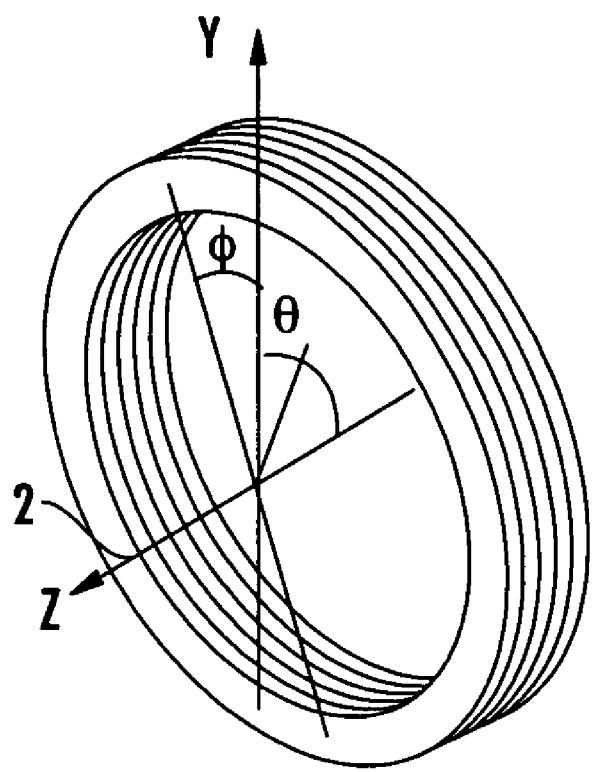
FIG. 3 is a drawing depicting the coordinates r, z, θ, φ used to define a projection plane data format.

According to one embodiment, the sorter 34 defines the coincidence events conversion to sinogram space with respect to a projection plane format using four variables, r, z, θ, and φ. As shown in FIG. 2, the variables r and φ identify a plane 24 that is parallel to the central Z axis 2 of the detector, with φ specifying the angular direction of the plane 24 with respect to a reference plane (defined as the Y-Z plane in FIG. 3) and r specifying the distance from the central Z axis 2 to the plane 24 as measured perpendicular to the plane 24. As further shown in FIG. 3, the variable θ defines an axial view angle parameter measured from the Y-axis. The variable θ is used to define coincidence events involving detector crystals from different rings. The value of θ varies according to the separation distance of the two rings which detected a particular coincidence event. The value z specifies the location in the z direction of the midpoint between two different detector rings detecting a coincidence event.

The projection plane variables, r, z, θ, and φ define the possible propagation paths taken by a pair of oppositely traveling gamma rays from an annihilation event to a pair of detector crystals 21. These propagation paths are commonly referred to as "lines of response" (LORs). Coincidence events occur at random, and the projection plane variables r, z, θ, and φ can be used to sort or organize the coincidence events according to LOR, i.e., the direction of the gamma rays which generated the coincidence event. Ultimately, the coincidence events can be stored in a histogram organized in a logical order based on the projection plane variables r, z, θ, and φ which define the LORs.

As will be appreciated by those skilled in the art, the sorter 34 can generate output data in other data formats, such as a set of sinogram arrays using only the variables r, φ and z. In such case, the result histogram, i.e., the histogram containing all the data from the scan, could be in the form of a three-dimensional array based on the variables r, φ and z. For a detailed description of an example of a sorter, reference is made to U.S. Pat. No. 5,272,343 entitled "Sorter for Coincidence Timing Calibration in a PET Scanner."

The sorter 34 can additionally perform the function of generating a histogram cell address for each coincidence event in the form of a byte offset from the base address of the result histogram memory. Each histogram cell address corresponds to a histogram cell. As one example, the histogram for a set of projection planes could represent a four dimensional array with coordinates (r, z, θ, φ), where "r" is the fastest changing index and "φ" is the slowest changing index. According to one example, suppose r', z', θ', and φ' represent the number of elements per index, respectively, for the four-dimensional array (r, z, θ, φ), where r'=250, z'=24, θ'=23, and φ'=210. The cell address corresponding to r=5, z=2, θ=3, and φ=4 can be computed, for example, as: histogram cell address=[(4*23*24*250)+(3*24*250)+(2*-250)+5]*(number of bytes per cell). The generic formula for the histogram cell address would be: [((φ*θ'*z'*r-')+(θ*z'*r')+(z*r')+r)]*(cell size).

The sorter 34 outputs a stream of histogram event packets, where each histogram event packet typically includes at least the following information: (a) a cell operation, e.g., increment by 1 or decrement by 1; and (b) a histogram cell address. According to one embodiment, a histogram event packet comprises a 29 bit stream where the first bit indicates the binary operation "increment by 1" or "decrement by 1," and the subsequent 28 bit stream represents the histogram cell address. According to another embodiment, a histogram event packet can comprise a 32 bit stream where the first four bits indicate an increment value of 1 though 8 or a decrement value of 1 through 8, followed by a 28 bit stream representing the histogram cell address.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

In one embodiment, system 1 includes a device for data storage, for example, a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, a CD-ROM, a DVD or an other digital source such as a network or the Internet, as well as yet to be developed digital means. In another embodiment, the computer executes instructions stored in firmware (not shown). Generally, a processor is programmed to execute the processes described herein. Of course, the methods are not limited to practice in PET and the herein described methods and apparatus can be utilized in connection with many other types and variations of imaging systems such as a combined PET/CT system. In one embodiment, the computer is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, field programmable gate arrays (FPGA), and other programmable circuits. Although the herein described methods are described in a human patient setting, it is contemplated that the benefits of the invention accrue to non-human imaging systems such as those systems typically employed in small animal research. In general, the methods described herein can be applied to a plethora of event counting systems and would be notably advantageous for those counting systems that have many potential event types but sparse and 'low count per event type' results.

In the PET imaging context, it is conjectured that the random coincidence event stream must be reordered to achieve cost effective TOF Reconstruction performance. It is also hypothesized that an ordered list can efficiently be generated from a set of compressed TOF sinograms.

The method for producing the compressed TOF sinograms for a PET coincidence stream greatly leverages:

1. Zone Cache Histogramming (ZCH) technique described in the ZCH publication published on IP.com as IPCOM000133358D.

2. U.S. Pat. No. 6,215,903 B1 (the RIVN compression algorithm)

3. A file system that supports large files (greater than 2 GBs)

The herein described methods and apparatus can be viewed as an extension to the Zone Cache Histogramming (ZCH) process. Simply put, the "flush of a Zone Buffer" phase of the ZCH method will be modified to add steps that include file read of an intermediate partial histogram that is compressed, decompress, cache efficient read-modify-writes histogramming, recompress, and write back to file.

To aid the description, an overview of PET coincidence "brute force" event histogramming and an overview of Zone Cache Histogramming will be first be given.

PET Acquisition "Brute Force" Histogram Implementation Overview

Figure 5:
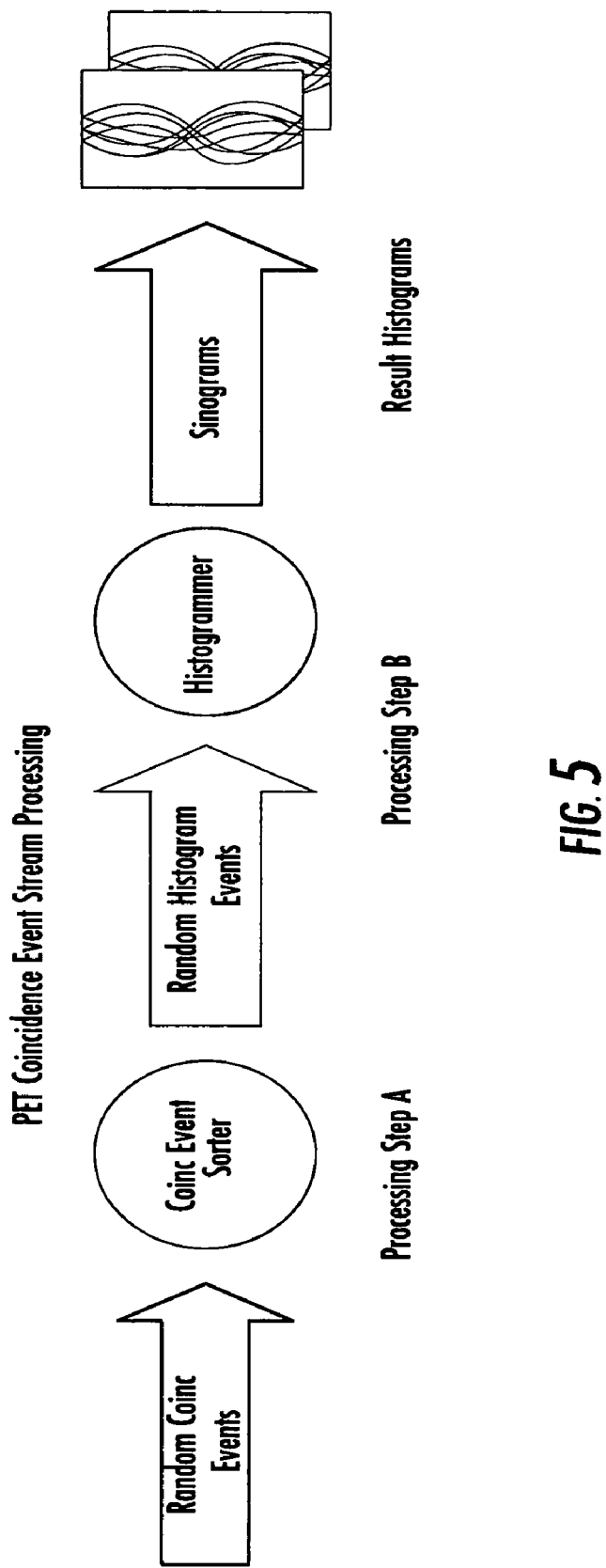
FIG. 5 illustrates a PET acquisition process that will nominally include the capture and conversion of a coincidence event stream.

A PET acquisition will nominally include the capture and conversion of a coincidence event stream such as depicted in FIG. 5.

The front-end detection of positron emission events and the selection of the emission events that are in coincidence are not shown in FIG. 5 since it is not pertinent to the discussion. In FIG. 5, "Processing Step A", the Sorter module consumes the random coincidence events from the stream produced by the not shown coincidence processor. The event rate presented to the sorter module can exceed 15 million events per seconds, which would exceed the modern day single CPU computer histogramming capability when the conventional brute force approach of histogramming is employed. The Sorter module converts the coincidence events from detector space to histogram address events that represent addresses of Line Of Responses (LORs) of a set of sinogram-based histograms. Each coincidence event represents the identification of the detector crystal pair that picked up a 511 keV gamma associated with a given positron emission in a specified coincidence window of time. The output of the Sorter module is a list of histogram address events that should be incremented (or decremented) for a sinogram based Result Histogram. The Sorter output mirrors the randomness of the coincidence stream, i.e. there has been no event re-ordering performed. Step B of the stream processing consists of the rudimentary read-modify-write back with optional test for overflow operations associated with histogramming. It is not uncommon for the set of Result Histograms for PET imaging to exceed a hundred megabytes (gigabytes if TOF), which would dwarf the typical computer L2/L3 cache memory size.

Zone Cache Histogramming Overview

The Zone Cache Histogramming technique divides the Result Histogram that typically resides in the cheaper slower bulk system memory into N number of zones (regions) and instantiates a corresponding "zone buffer" for each of the histogram zones. This is illustrated in FIG. 6.

Figure 6:
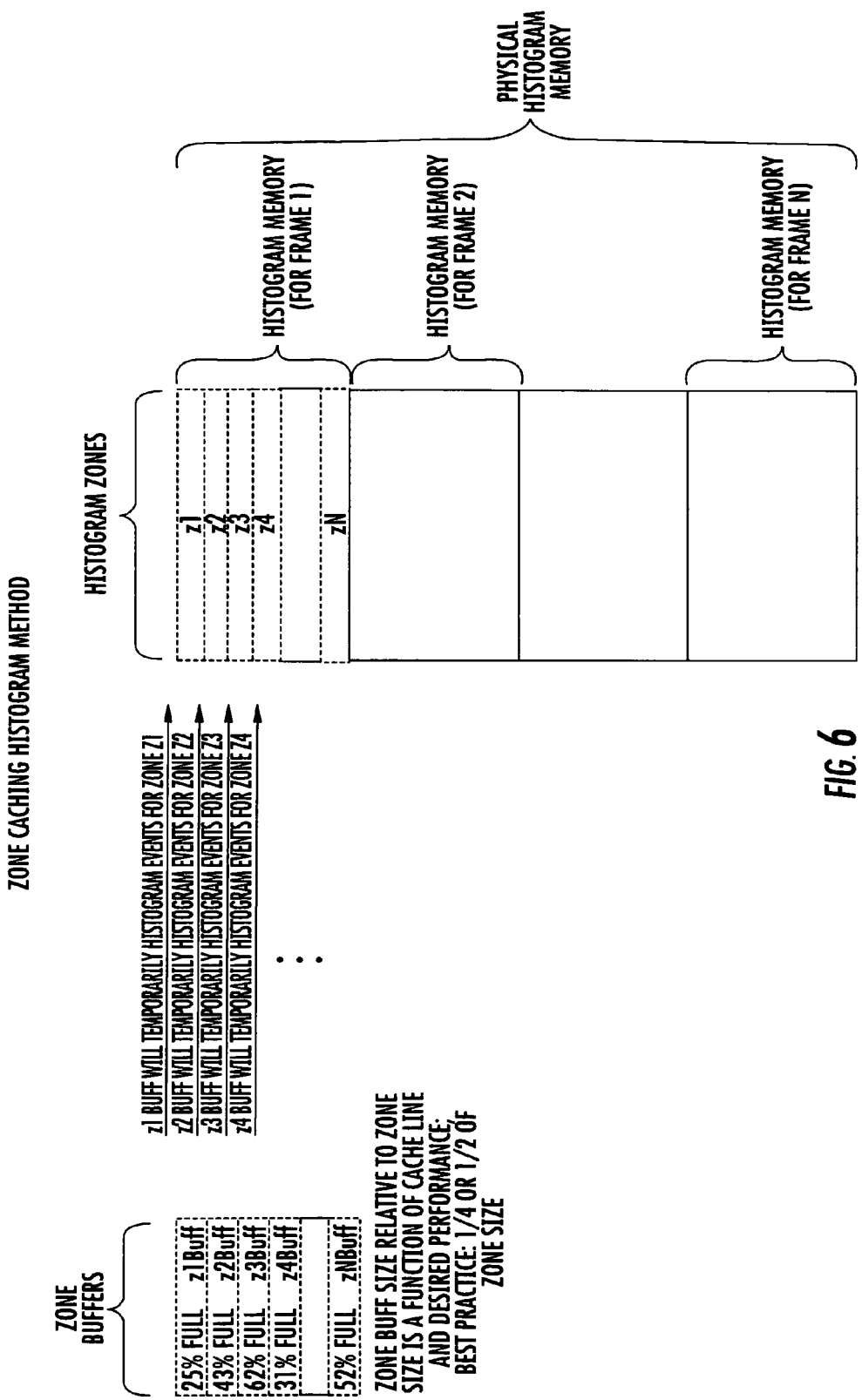
FIG. 6 illustrates a Zone Cache Histogramming technique that divides the Result Histogram that typically resides in the cheaper slower bulk system memory into N number of zones (regions) and instantiates a corresponding "zone buffer" for each of the histogram zones.

The "Zones" are represented in FIG. 6 as "z1", "z2", "z3", ... "zn"; the "Zone Buffers" are represented as "z1Buff", "z2Buff", "z3Buff", ... "znBuff".

Figure 7:
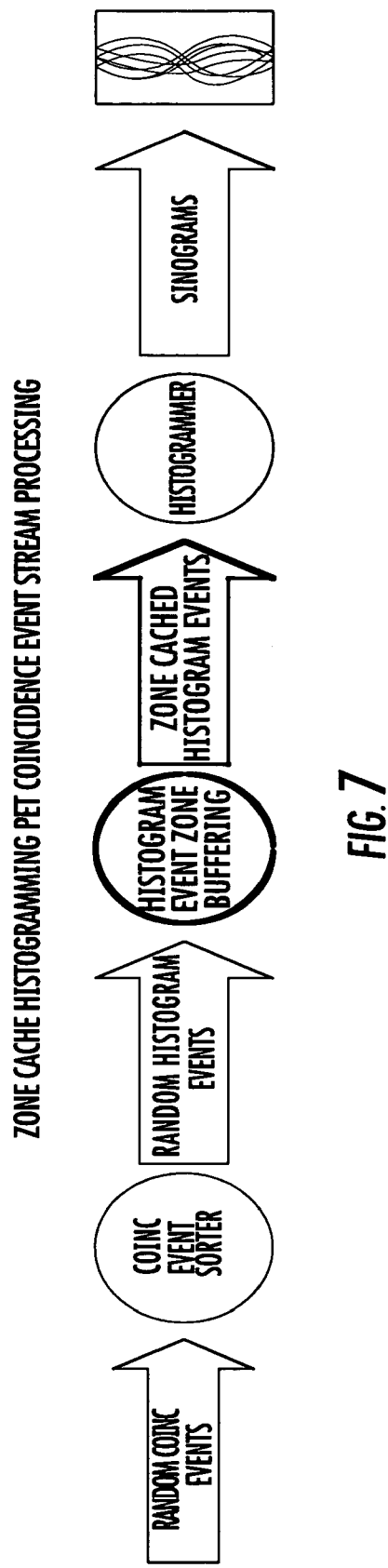
FIG. 7 illustrates a "Histogram Event Zone Buffering" phase of the revised PET Coincidence Event Stream.

To achieve histogramming performance, each zone must represent a region that is sized to be equal to or smaller than the size of the faster L2/L3 cache memory. An intermediate step of placing the histogram cell address into the corresponding zone buffer is then added to the histogramming process. This new processing step is depicted as the "Histogram Event Zone Buffering" phase of the revised PET Coincidence Event Stream flow depicted in FIG. 7.

Figure 8:
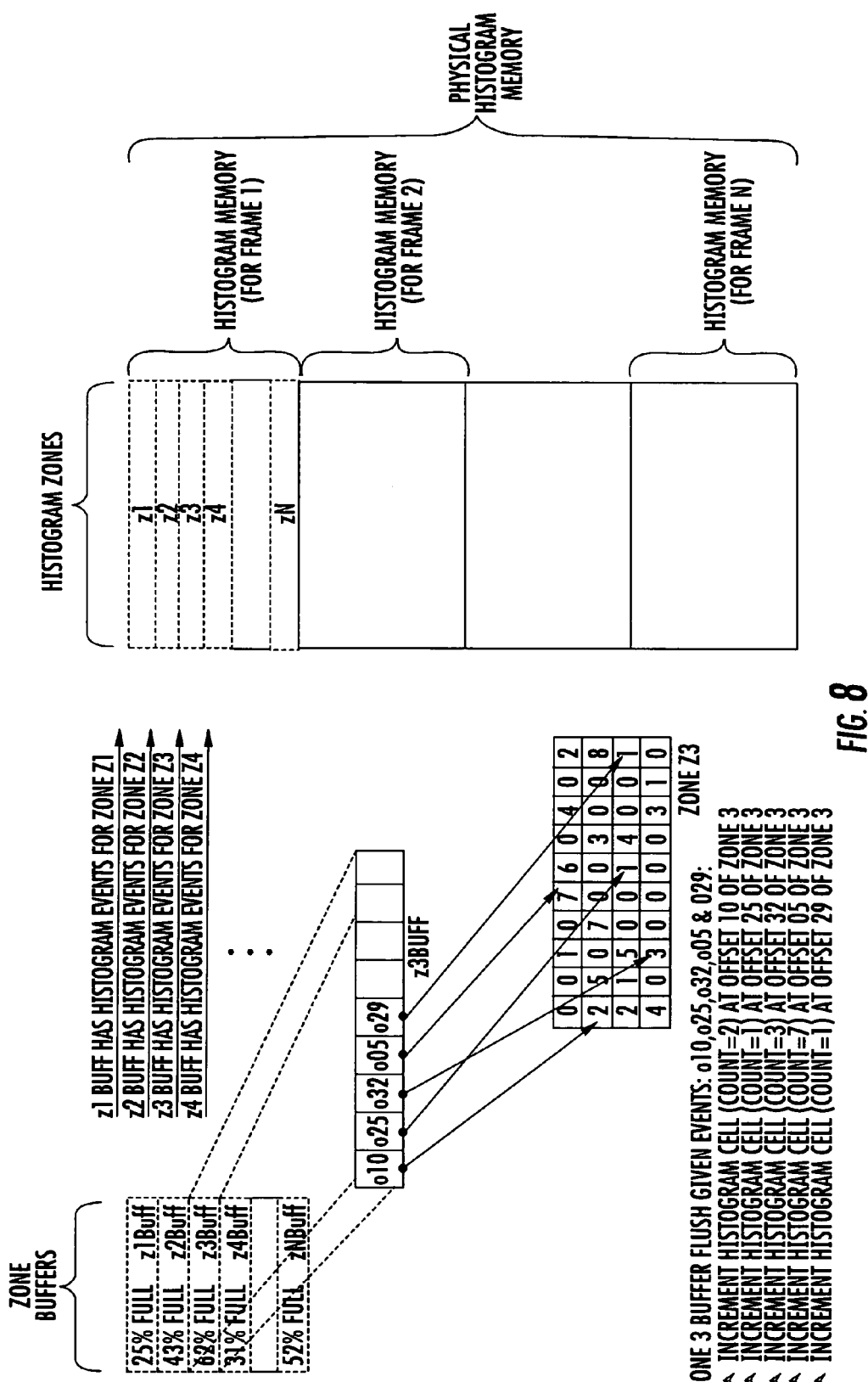
FIG. 8 illustrates that a PET acquisition "frame" pertains to the event histogramming associated for the detector for a period of time, and that once a frame is acquired per the operator specified frame time, the Sorter immediately switches to a new frame.

A more detailed rendering of the Zone Buffers and the "flush" processing associated with the Histogram Event Zone Buffering phase is depicted in FIG. 8.

The zone buffers are sized such that sufficient events for the zone are accumulated before an efficient "cache optimal" sequence of read-modify writes is performed. When a zone buffer is filled, the zone events are flushed to the result histogram (i.e. histogrammed) resulting in the memory associated with the result histogram being pulled into cache, which leads to cache hits and an increase in histogramming performance.

It should be noted in the context of the PET acquisition application that the set of Zone Buffers would only pertain to histograms for the "active" frame. A PET acquisition "frame" pertains to the event histogramming associated for the detector for a period of time. Once a frame is acquired per the operator specified frame time, the Sorter immediately switches to a new frame. These frames are depicted in FIG. 8. To minimize memory usage, only one set of Zone Buffers for the current active frame is employed.

Zone Cache Histogramming Optimizations Applicable to Producing Compressed TOF Sinograms Several techniques for optimizing the ZCH performance are described in the previously mentioned ZCH publication (IP.com). Optimizations notable and applicable for efficient production of compressed TOF sinograms from a live coincidence event stream include:

1. Use of the high order Histogram Event Address bits as a simple Zone ID.

2. Minimizing the Zone size to less than $2^{**16}$ (65536) bytes to minimize Zone Buffer memory.

3. Having Zone Buffer "spares". And

4. Multi-threaded implementation.

The aforementioned ZCH publication discusses these performance optimizations in more detail.

Description of "Production of Compressed TOF Sinograms for Live Coincidence Event Stream"

Note: The use of the term "sinograms" herein includes histograms that are either sinogram or projection view based.

The herein described methods and apparatus assume a software based PET Acquisition "Sorter" implementation running on a computer that has a file system that supports large (hundreds of gigabytes) files. Prior to the PET acquisition, a file (preferably on a local file system that has good read/write performance) is allocated for each set of histograms associated with a "frame" of a PET scan. This file will be referred to as the "Histogram with Compressed Zones File" or HCZF file and minimally have a header and format representative of FIG. 9, in one embodiment.

In one embodiment, one aspect is to have the histograms mapped to HCZF files instead of being mapped to physical memory. Like the Zone Cache Histogramming technique, the histograms are subdivided into equal length "Zones". But unlike the physical memory mapped Histogram Zones, the Zone data in the file is in a compressed state.

The compression algorithm is somewhat arbitrary, but for "live" PET coincidence stream histogramming, an algorithm that yields high PET raw data compression on small data segments and requires low CPU overhead is favored. The RIVN algorithm (U.S. Pat. No. 6,215,903 B1) is ideal. However, it is contemplated that the benefits of the invention accrue to methods and apparatus that use other compression algorithms. The herein described coupling of ZCH and RIVN technologies produces "intermediate" compressed sinograms that minimizes dependency on physical memory, and this is just one technical effect.

In one embodiment, the collection of compressed zones would have a corresponding Compression Vector Table (CVT). The CVT is a table of offsets and sizes, indexed by the Zone ID. CVT entries facilitate quick indexing to find the byte offset within the HCZF file for a given Zone, and its corresponding size of compressed data. The CVT would logically be "in memory" during the histogramming associated with the frame for ease of reference and performance, but could be written to the head of the HCZF file (as suggested in FIG. 9) at a frame switch time to allow "batch" or "post-acquisition" condensing (gap elimination) of the compressed vectors.

Figure 9:
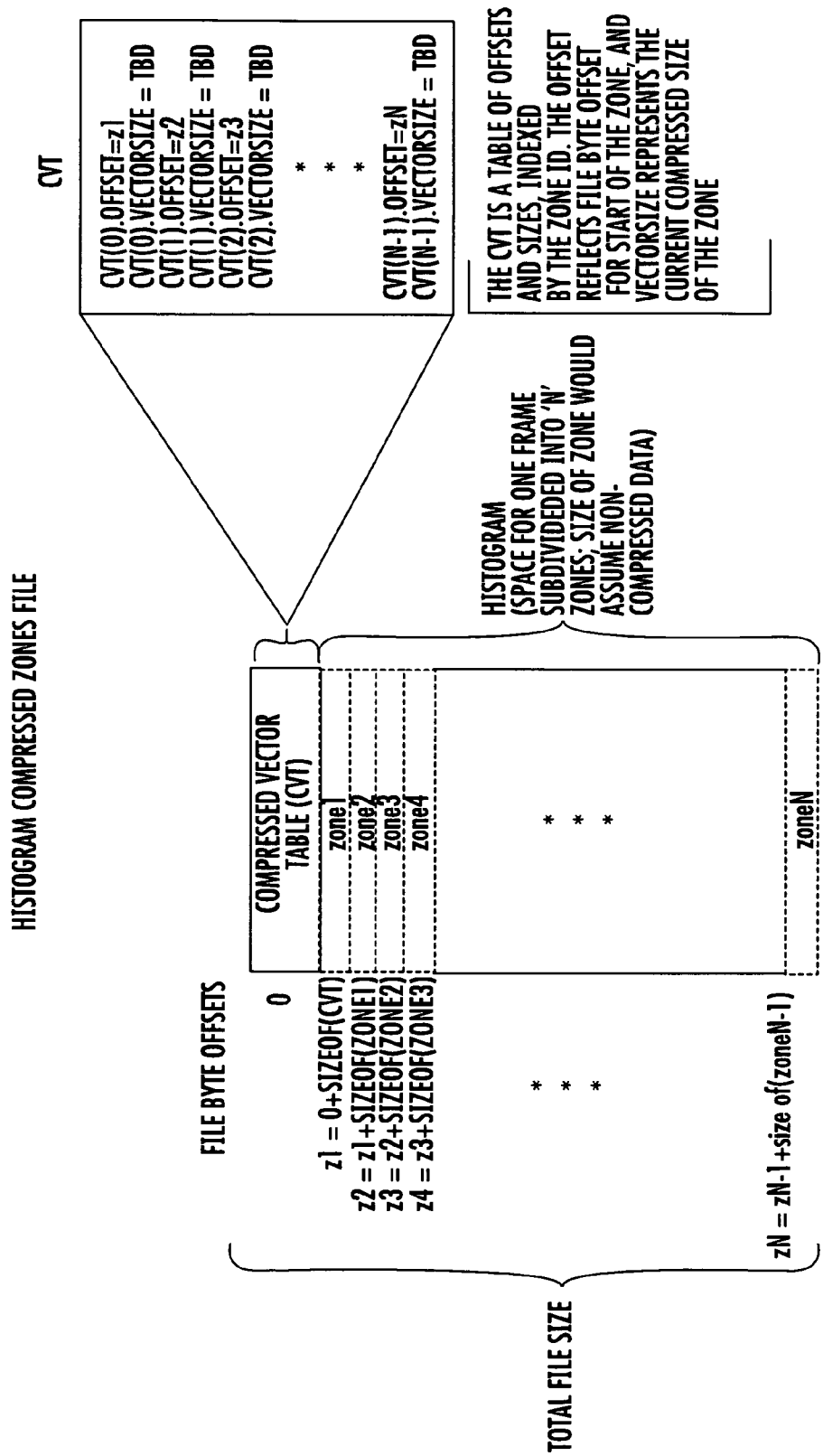
FIG. 9 illustrates a file that is referred to as the "Histogram with Compressed Zones File" or HCZF file.

FIG. 9 suggests that the HCZF space allocated for a Zone assumes the data will be uncompressed. This is to guarantee enough space for the Zone data regardless of its live intermediate levels of compression. It is assumed that the compressed data will be equal to or smaller than the uncompressed data. Note that the data associated with a given Zone may be uncompressed, updated, and recompressed several times during the course of an acquisition. However, for some applications (including PET imaging) the HCZF space allocated for a Zone could be less the uncompressed size if the worst-case compressed data allows. This optimization would lead to less file 'seeking' and/or reduce the file footprint for direct I/O or virtual file embodiments of the method.

In one embodiment, the histogramming Zone Buffer "flush" phase of the Zone Cache Histogrammer (reference FIG. 8) would be modified to have the sequence of steps identified below in TABLE 1.

TABLE 1

| | |
|---|---|
| 1 | Index into the CVT for the zone corresponding Zone Buffer and get HCZF file offset and current length of the compressed zone data. (Note: initially the size of the zone data would be zero, indicating no events have been histogrammed for the zone.) |
| 2 | Seek to the zone's file offset, and read from the file into a memory the current compressed data associated with the zone. |
| 3 | Uncompress the zone data. |
| 4 | For each event in the Zone Buffer, perform the rudimentary read-modify-write back operations associated with event histogramming. |
| 5 | Compress the updated zone data. |
| 6 | Write the compressed Zone Data back to the HCZF at the appropriate zone offset. |
| 7 | Update the CVT vectorSize for the zone. |

Note that only Step 4 of Table 1 was performed for the original ZCH Zone Buffer flush as described in the aforementioned ZCH publication.

Performance Factors

The performance is a function of the following Factors:
a) Size of the Zone Buffers
b) Counts Density of the histogram Zone Data
c) Count Rate of the event stream
d) Computer Performance
e) File System Performance It is intuitive that the larger the Zone Buffers, the fewer times the "flush" function will have to be invoked. The size of the Zone Buffers can be driven by the number of Histogram Zones (indirectly related to prescribed histogram size) and the amount of physical memory allocated for Zone Buffers.

The Count Density of the Zone Data can be equated to the average counts per histogram cell. The lower the Count Density, the greater compression (reduction in size) of the Zone Data, which reduces the file input/output of the "flush" function. Furthermore, it has been demonstrated that the RIVN compression algorithm yields not only high compression for low Count Density, but requires increasingly less CPU overhead as the Count Density decreases. The RIVN algorithm excels at finding and elimination of zeroes.

The Count Rate of the stream will directly drive the frequency of the Zone Buffer "flushes". For a PET Scan, the real time coincidence event Count Rate can range from a few KCPS to 10-15 MCPS. It should be noted however that the vast majority of studies are accomplished with less than 1 MCPS. In addition to live scanning, it is appropriate to also consider the retrospective unlisting of a coincidence stream. In the unlisting scenario, the Count Rate is more appropriately based on maximum events that can be unlisted from file per second. A high performing unlist to Compressed TOF Sinograms process would be advantageous for rebinning the data as a precursor to the image reconstruction.

The performance of the computer that is being used as the PET acquisition "sorter/histogrammer" is an important critical factor for a good implementation of the herein described methods an apparatus. The greater the number of CPUs, CPU frequency and cache size, correlates to greater performance.

The File System Performance will affect the Zone Buffer "flush" time. The file read/write capability should be considered, and in addition, the buffering of I/O. It is speculated that a non-buffered file system (a.k.a. Direct or Raw I/O) will yield the best performance for scenarios that have high Count Density and large Histogram Size since it will not contend for system memory (one of the advantages of the herein described methods and apparatus). Most PET scans result in widely distributed events in histogram space but it is acknowledged that some distributions may benefit from buffered I/O. In fact, the vast majority of the clinical frames of compressed TOF and/or gated sinogram data will result in data sets that are a few percent in size of the uncompressed data. Thus, it might be advantageous to have a HCZF file Zone allocations that are more closely matched to the expected final size of the compressed data and if the allocated space is insufficient, dynamically allocate a larger space within the file. This approach could minimize the seek latencies (one concern depending on implementation) and benefit significantly from buffered I/O. This is an area where trial and error may be employed to find the best match to the computer hardware.

Controlling the Count Density of the Histogram Zone Data to Maximize the Compressed TOF Sinogram Histogrammer Performance Since the intermediate histogram data compression/decompression times and data sizes increase as the Count Density increases, it may be required to "reset" the Zone counts periodically. It is proposed to extend the HCZF file approach to allocate space for a new Zone in the file each time the Count Density for a given Zone exceeded a threshold, and to keep track of the data that had reached the threshold in a linked list construct. In one embodiment, each node of the Linked List would at a minimum contain:

1. Zone ID.
2. HCZF file offset of the Zone Data that reached the Count Density threshold. And
3. Size of the compressed Zone Data.

The Zone Buffer "flush" logic would then be extended after the write back step (reference Steps 6 & 7 of Table 1) processing would be as follows:
1. If Zone Count Density greater than threshold, then Append the Zone ID, Zone Offset and compressed data size to the "Threshold Met Zones" Linked List, Allocate new space for the Zone at end of the HCZF file, Update the CVT for the Zone to point to new Zone offset, and set size of compressed Zone data to zero.
2. End if
3. At the end of the acquisition (at frame switch time) append the Linked List of Threshold Met Zones to the end of the HCZF file and update a header to point to the Linked List.
4. At frame switch time (or when spare CPU cycles exist), a batch job would be kicked off to process the "Threshold Met Zones" Linked List. For each node in the linked list, the Zone data would be decompressed and summed cell to cell with a master or accumulated data set for the Zone. Then compressed and rewritten back to the HCZF or the frame's final Raw Data File (RDF).

Controlling the Count Density of the histogram Zone Data to maximize the compressed TOF sinogram histogrammer performance is implemented in one embodiment.

Post Acquisition Processing Potentially Reduced

One potential side benefit includes the reduction of the post-acquisition work presently accomplished by the "frame saver" thread wherein a "frame saver" thread is logic to take the data that was produced by the Sorter/Histogramer and 'finalize or complete it' into its Raw Data File (RDF) format desired for hand-off to the image reconstruction process. 'Frame Saving' is done after the acquisition period of the frame has completed. It is usually a lower priority than sorting/histogramming for the 'next frame' (i.e. 'frame saving' can be a batch job). The desired Raw Data Files (RDFs) file format is Compressed TOF Sinograms, which is a comparable format as to the HCZF file, including a similar CVT. The primary difference is the compressed histogram data is indexed by sinogram or projection view versus the Zones described herein.

At end of acquisition (frame switch), the "frame saver" thread RIVN compresses the histogram in memory and writes the compressed data to the corresponding RDF.

In the HCZF scenario, the frame saver would not have to compress the majority of the data (assuming a small Thresholds Met Zones linked list), but merely move the compressed vectors from the HCZF file to the RDF, effectively eliminating the gaps between the compressed Zone data to achieve the smallest RDF possible. Some minor decompress/recompress would have to be performed at the Zone boundaries to restructure the data along sinogram/projection boundaries. Note that the RIVN algorithm works on segments of 4 KB, so only the 4 KB segment at a Zone or sinogram boundary would potential have to be decompressed, split and recompressed.

An Example to Illustrate the Process and Expected Performance

Assume a live PET TOF Static Scan (single frame/acquisition per scan) and:
1. A frame with a histogram of 64 million LORs (Lines Of Response).
2. A TOF spectrum per LOR of 256 bins.
3. Byte mode histogram cells (one byte per cell).
4. A coincidence Count Rate of 10 MCPS.

The histogram size based on this scan prescription assumption would be: Histogram Size=64 M LORs X 256 TOF bins X one byte per cell=16 GB.

Further assume the following implementation:
1. A histogram Zone size of 32 K cells.
2. 8 GB of physical memory allocated for Zone Buffers.
3. 2 bytes per event in Zone Buffer (store only LS 15 bits of histogram address & rely on Zone ID in ZoneBuffer).
4. A compress/decompress capability of 160 MBS or greater for Zone data Count Density less than 0.1 counts per cell.

The number of Zones and corresponding Zone Buffers would equal:

Number of Zones=Number of Zone Buffers=Histogram size of 16 GB/32 K cells=512 K.

The Zone Buffer size and Max Events per Zone Buffer would equal:

Zone Buffer size=8 GB physical memory/512 K Zones=4 KB.

Max Events per Zone Buffer=4 KB/2 bytes per event=2 K events.

At steady state, assuming events evenly distributed across the histogram, we derive the following:

Average time to fill a given Zone Buffer=2 K events per Zone Buffer/(10 MCPS/512 K Zones)=102.4 seconds.

Zone Buffers filled per sec=512 K Zones/102.4 seconds=5120.

From the 5120 Zone Buffers filled per second rate we can deduce that 160 MB of histogram data (5120×32 KB per Zone) must be decompressed and recompressed per second. It is speculated that this required performance is achievable with ZCH and RIVN compression on Sorter computer hardware comparable to that deployed for at least one existing PET scanner if the Count Density of the Zone Data was controlled to be less then 0.1 counts per cell. In defense of this argument, the following data point is offered. The scanner deploys ZCH histogramming and RIVN compression and can sustain a 10 MCPS Count Rate for a 1-sec per frame 3D Dynamic Scan for the high-resolution detector (that has just short of 64 M LORs). The 10 M counts distributed across 64 M LORs equates to a Count Density of 0.15. Although there is no significant file seeks or decompressing associated with the work associated with this data point, 64 MB of histogram with a Count Density of 0.15 is being compressed and written to file while Sorter and Histogrammer are handling a 10 MCPS Count Rate. Also note that RIVN decompression is faster (requires less cpu instructions) than compression.

At 10 MCPS for 16 GB of histogram cells, it would take on the average 160 seconds to achieve a Count Density of 0.1 counts per cell. A three minute acquisition at 10 MCPS would potentially have to reset the Zone Data counts one to two times if the Count Density threshold for reset was 0.1. It is speculated that most clinical scans under 5 minutes of acquisition times would not require the intermediate Zone Data counts to be reset since most clinical scans have a Count Rate of less than 1 MCPS.

Note that the Zone Buffer "flush" would not necessarily have to rely on compressed Zone Data if the file system performance was high enough to handle the Zone Buffers fill rate. In the 10 MCPS example the file I/O associated with a non-compressed flush would require a combined 320 MBS read/write (160 MB read, histogram update and 160 MB written back, all accomplished in one second). The RIVN compression algorithm however allows a lower performing file system, since the time to compress and write compressed data to file on a lower performing file system is nominally less than the time to write uncompressed data, and likewise for decompressing.

Advantageous for Gated and Fast Dynamic Scans

With the premises and assumptions of the simple example, it was conjectured that given 8 GB of RAM and a sorter comparable to an existing sorter, the sorter could handle a live 10 MCPS sort, histogramming and production of a 16 GB compressed TOF sinogram for all acquisitions regardless of length of acquisition.

If we take those same assumptions (10 MCPS Count Rate, 32 KB Zone Size, 8 GB of RAM available for the Zone Buffers, etc.) but in the context of a Gated Scan that has 10 bins, the total Histogram size would be 160 GBs (vs. 16 GB) and the number of Zones and Zone Buffers would also increase by a factor of 10. The 8 GB of RAM available for the Zone Buffers assumption would translate into a 10× decrease in the events per Zone Buffer and Zone Buffers filled per sec. In this scenario, the system would most likely not be able to maintain a live stream of 10 MCPS. But on the positive side, the 10 MCPS Gated Scan of 10 bins would translate into a 10× slower rate of achieving the 0.1 Count Density, which thus results in more efficient decompression/compression and higher level of compression. But on the negative side, the smaller Zone Buffer sizes means that the histogramming associated with the flush would be less cache efficient. Options to handle the Gated Scan scenario with the fixed allocation of Zone Buffer memory would include, but not be limited to, lowering the target Count Density threshold for resetting the Zone Data, reducing the maximum supported incoming Count Rate for a "live" sort to sinogram space, or listing the 10 MCPS event stream to file and then unlisting to the Gated scan prescription as a 'batch job'. Unlisting a high count rate event stream as a batch job might require longer to process than acquisition of the live scan, but would allow the full desired LOR/TOF/Gated Bins fidelity with the allocated physical memory and still only require a single processing pass of the event stream, and note that the batch unlist Gated Scan could be initiated during the "live" acquisition of the list file to reduce the total time for acquiring the data and producing the compressed sinograms.

The conclusion that is drawn is that as the number of gated bins and/or TOF bins increase, the RAM required to maintain a max count rate does not necessarily have to increase.

For most Gated Scans it is speculated that all bin data would already be compressed and ready to be compacted (inter-Zone gap eliminated) into a RDF at the end of the acquisition.

Comparable arguments can be made for Fast "1 second" Dynamic Scan framing, with comparable trade-offs for acquiring in word mode, and/or separate Delays. It should be noted however, that the number of Zone Buffers required to facilitate a fast frame switch may be twice as many since the partially filled Zone Buffers for the just acquired frame would have to be flushed.

Technical Effects Also Include the Following

1) Significantly reduces the amount of physical memory required to do PET TOF (and non-TOF) sinogram based histogramming for all scan modes, including Gated Scan and Dynamic Scan.

2) Serves as a TOF image reconstruction accelerator by presenting the TOF events in a sinogram/projection LOR order (or ordered list).

3) Maintains the TOF online raw data storage capacity and archive media consumption at comparable non-TOF levels. It is conjectured that the size of a compressed TOF sinogram for a given emission is only a few percent larger than the non-TOF compressed sinogram.

4) Maintains "status quo" for raw data network/archive performance. The standard raw data archive would still be compressed sinograms vs. List Files.

Other Technical Effects and Points of Novelty Include a) Use of histogram mapped into files versus physical memory to reduce the amount of RAM required for a PET computer based Sorter/Histogrammer.

b) Technique of compressing the sub-region of the intermediate histogram and storing the intermediate compressed results in a file (versus RAM) to reduce the amount of RAM required and allow a lower performing file system for a PET computer based Sorter/Histogrammer.

c) Concept of controlling the Count Density of intermediate compressed histograms by adding the compressed histogram (or sub-region of histogram) to a link list and then resetting the histogram to zero counts as a means of sustaining a high Count Rate associated with a live or unlist stream.

d) Combination of Zone Cache Histogramming and Patented RIVN compression algorithm to aid production of compressed PET Time Of Flight sinograms.

e) Concept of using compressed PET Time Of Flight sinograms as an input data format and accelerator for TOF image reconstruction.

f) Concept of producing a list of order LOR events from compressed TOF sinograms for a list mode reconstruction implementation.

g) Compressed PET Time Of Flight sinograms as efficient means for PET Scanner online raw data storage, and enabler for high performance network/archive of PET raw data.

h) Technique for maximizing count rate capability for live or unlist PET scans where sinogram/projection view based output histograms are desired.

i) Concept of using Buffered I/O file system in conjunction with intermediate compressed low Count Density PET histograms to minimize file seeks and file I/O.

j) The processing of a list of events in a single pass, wherein the list has at least one million events. Or a list with at least 10 or 60 or 100 million events. The resultant histogram may or may not include PET TOF information.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A PET system comprising:
an imaging volume configured to receive an object to be scanned;
at least one gamma camera positioned to receive a plurality of gamma rays emitted from the object; and
a computer coupled to the gamma camera, said computer configured to:

generate a first set of sinogram data corresponding to the plurality of gamma rays;
compress the first set of sinogram data;
store the compressed sinogram data in a file;
read the compressed sinogram data from the file into memory;
generate a second set of sinogram data corresponding to the plurality of gamma rays;
decompress the compressed sinogram data;
modify the decompressed sinogram data based on the second set of sinogram data;
recompress the modified decompressed sinogram data;
write the recompressed sinogram data from memory to the file;
generate a compressed PET time of flight (TOF) sinogram corresponding to the recompressed sinogram data; and
reconstruct a TOF image using the compressed PET TOF sinogram.

2. A system in accordance with claim 1 wherein said computer further configured to use a RIVN based compression algorithm.

3. A system in accordance with claim 1 wherein said computer further configured to use a RIVN based compression algorithm and a ZCH algorithm.

4. A system in accordance with claim 1 wherein said computer further configured to produce a ordered list of LOR events from the compressed PET TOF sinogram.

5. A system in accordance with claim 4 wherein said computer further configured to use the ordered list to perform a list mode reconstruction.

6. A system in accordance with claim 1 wherein said computer further configured to store the compressed PET TOF sinogram in the file.

7. The PET system of claim 1 wherein the computer is further configured to:
define a plurality of sub-regions corresponding to the first set of sinogram data; and
store the compressed sinogram data in a plurality of files, each of the plurality of files corresponding to a respective sub-region.

8. The PET system of claim 7 wherein the computer is further configured to store informational data corresponding to the compressed sinogram data in an indexed table.

9. The PET system of claim 8 wherein the informational data comprises at least one of byte offsets and sizes indexed by sub-region.

10. The PET system of claim 1 wherein the computer is further configured to use a buffered I/O file system.

11. A method comprising:
detecting gamma rays emitted from an object;
generating a histogram corresponding to time of flight (TOF) data of the gamma rays;
compressing the histogram;
storing the compressed histogram in a file;
reading the compressed histogram from the file into memory;
modifying the compressed histogram;
writing the modified compressed histogram from memory to the file; and
creating a compressed TOF image based on the modified compressed histogram.

12. The method of claim 11 further comprising compressing the histogram using a RIVN based compression algorithm.

13. The method of claim 11 further comprising using a ZCH algorithm for intermediate histogrammer processing steps.

14. The method of claim 11 further comprising:
compressing a plurality of sub-regions of the histogram; and
storing each of the plurality of compressed sub-regions of the histogram in a respective file.

15. The method of claim 14 further comprising:
monitoring a count density of the plurality of sub-regions; and
creating a new sub-region of the histogram if the count density of one of the plurality of sub-regions reaches a predetermined condition.

16. The method of claim 14 further comprising generating an indexing table corresponding to the plurality of compressed sub-regions.

17. A computer readable storage medium having a computer program stored thereon and representing a set of instructions that when executed by a computer causes the computer to:
acquire initial time of flight (TOF) PET data;
compress the initial TOF PET data;
store the compressed TOF PET data in a file;
reacquire TOF PET data;
read the compressed TOF PET data from the file into cache memory;
decompress the compressed TOF PET data;
modify the decompressed TOF PET data based on the reacquired TOF PET data;
compress the modified TOF PET data;
store the modified TOF PET data in the file; and
create an image from the modified TOF PET data.

18. The computer readable storage medium of claim 17 wherein the computer is further caused to compress the initial TOF PET data using a RIVN based compression algorithm.

19. The computer readable storage medium of claim 17 wherein the computer is further caused to generate a histogram corresponding to the initial TOF PET data.

20. The computer readable storage medium of claim 19 wherein the computer is further caused to use a ZCH algorithm for intermediate histogrammer processing steps.

21. The computer readable storage medium of claim 17 wherein the computer is further caused to:
son the initial TOF PET data into a plurality of zones; and
store the initial TOF PET data in a plurality of files, each file corresponding to one of the plurality of zones.

22. The computer readable storage medium of claim 21 the computer is further caused to:
generate an index corresponding to the initial TOF PET data; and
continuously update the index based on real-time changes in the initial TOF PET data.

* * * * *

UNITED STATES PATENT AND TRADEMARK OFFICE
CERTIFICATE OF CORRECTION

PATENT NO. : 7,705,314 B2  Page 1 of 1
APPLICATION NO. : 11/447558
DATED : April 27, 2010
INVENTOR(S) : Cook et al.

It is certified that error appears in the above-identified patent and that said Letters Patent is hereby corrected as shown below:

On the Title Page, Item (54) & Col. 1 line 3, in the title, delete "COMPRESSION" and substitute therefore -- COMPRESSED --.

Col. 16, line 50 (Claim 21), delete "son" and substitute therefore -- sort --.

Signed and Sealed this

Twenty-ninth Day of June, 2010

David J. Kappos
*Director of the United States Patent and Trademark Office*